United States Patent [19]

Howe

[11] Patent Number: 5,329,939
[45] Date of Patent: Jul. 19, 1994

[54] HUMIDIFIER WITH LIQUID LEVEL CONTROL

[75] Inventor: Blair E. Howe, Rancho Santa Margarita, Calif.

[73] Assignee: Cimco, Inc., Costa Mesa, Calif.

[21] Appl. No.: 989,341

[22] Filed: Dec. 11, 1992

[51] Int. Cl.⁵ .................... A61M 16/00; H05B 3/20
[52] U.S. Cl. .................... 128/203.27; 128/203.12; 128/200.14; 222/56; 239/135; 239/379; 261/DIG. 4
[58] Field of Search .............. 128/200.14, 200.18, 128/200.21, 203.16, 203.17, 203.26, 203.27, 204.14, 203.12; 239/135, 139, 146, 338, 379; 222/56; 261/142, DIG. 4, DIG. 65

[56] References Cited

U.S. PATENT DOCUMENTS

| | | | |
|---|---|---|---|
| 1,972,962 | 9/1934 | Weber | 137/68 |
| 3,659,604 | 5/1972 | Melville et al. | 128/203.27 |
| 3,746,000 | 7/1973 | Edwards | 128/200.16 |
| 3,806,102 | 4/1974 | Valenta et al. | 261/142 |
| 3,892,235 | 7/1975 | Van Amerongen | 128/200.16 |
| 3,916,891 | 11/1975 | Freytag et al. | 261/141 |
| 4,036,919 | 7/1977 | Komendowski | 261/122 |
| 4,051,205 | 9/1977 | Grant | 261/70 |
| 4,113,809 | 9/1978 | Abair | 261/81 |
| 4,793,339 | 12/1988 | Matsumoto | 128/200.16 |
| 4,926,856 | 5/1990 | Cambio, Jr. et al. | 128/203.26 |
| 5,063,921 | 11/1991 | Howe | 128/200.14 |
| 5,139,016 | 8/1992 | Waser | 128/200.16 |

*Primary Examiner*—Edgar S. Burr
*Assistant Examiner*—Eric P. Raciti
*Attorney, Agent, or Firm*—Poms, Smith, Lande & Rose

[57] ABSTRACT

An adaptor is made to connect a standard sterilized water container to a standard aerosol flow passage that itself is connected to a heater. The flow control adaptor comprises a nipple that is connected to the water bottle above the heater and chamber and extends through and sealing relation to the chamber to position the nipple bottom at the heater platen which forms the bottom of the aerosol flow chamber. The bottom of the nipple adjacent the bottom of the chamber is formed with a relatively lower and smaller water feed aperture and a relatively higher and larger vent aperture that collective operate to maintain a constant level of water in the bottom of the aerosol flow chamber.

14 Claims, 4 Drawing Sheets

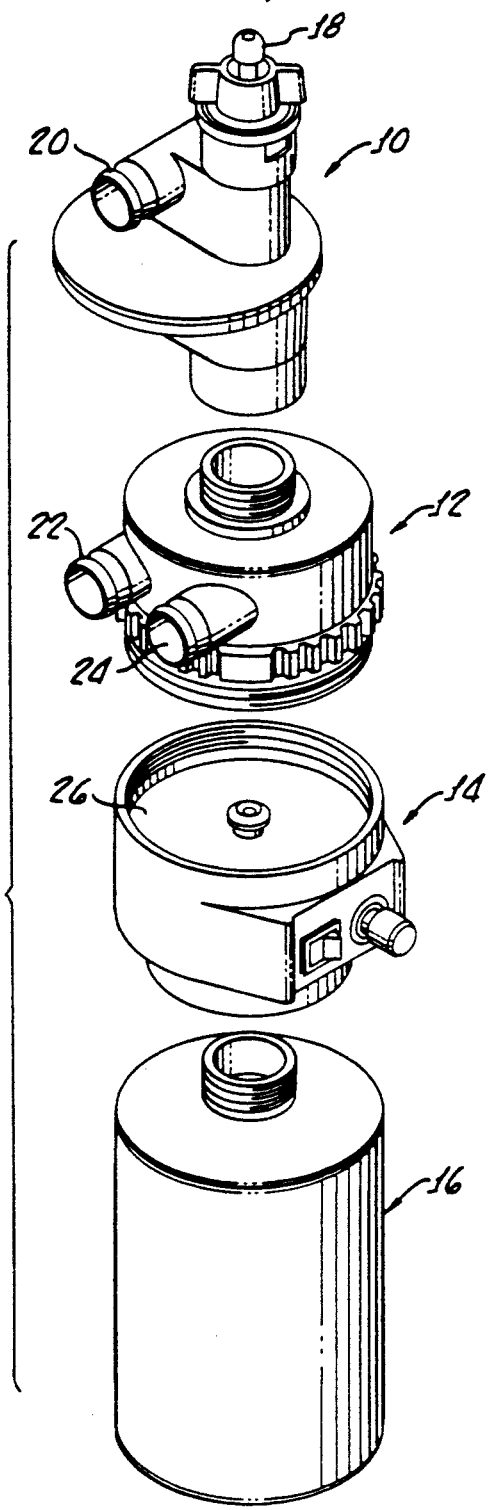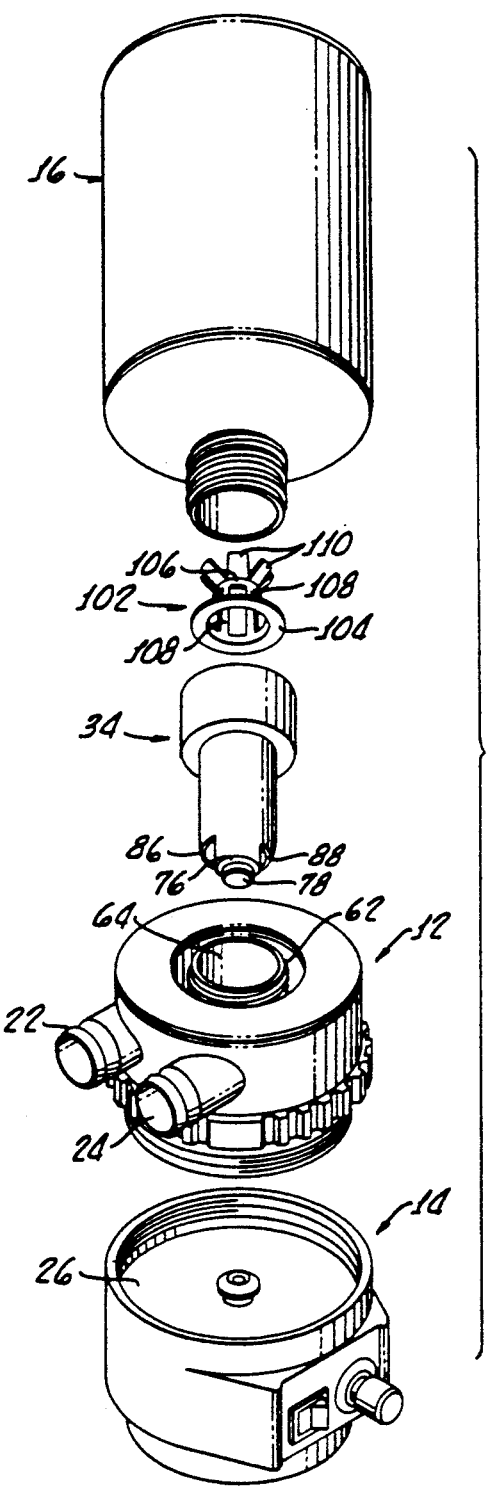

HUMIDIFIER WITH LIQUID LEVEL CONTROL

BACKGROUND OF THE INVENTION

The present invention relates to humidifiers for inhalation therapy, and more particularly concerns a humidifier arranged for use with a source of controlled breathing mixture to provide a humidified breathing mixture.

Hospital patients requiring relatively low flow rates of moisturized breathing mixture of higher oxygen content are often serviced by simple, disposable nebulizers or humidifiers. Such an inexpensive disposable nebulizer is disclosed, for example, in U.S. Pat. No. 5,063,921 to Blair E. Howe for Nebulizer Heater. In the arrangement of this patent, oxygen under pressure is mixed with air to provide a high speed turbulent air stream that entrains water from a water bottle and which is caused to flow through a flow control chamber and over a heater to provide a moisturized heated and oxygen enriched breathing mixture to the patient. However, some patients require higher flow rates of oxygen enriched air for purposes of therapy and cannot be serviced at such high flow rates by conventional nebulizers. Some patients require more complex and selectively variable flow rate control of breathing mixtures. Breathing mixtures of such high flow rates and/or variable control are generally provided in a hospital by complex and expensive equipment known as a ventilator.

Ventilators often involve microprocessor controlled systems, electrically powered and electronically operated. These systems may include connections to wall air and oxygen pressure, but also may include optional internal compressors to supply additional air requirements. Ventilator systems are capable not only of providing air for breathing by the patient but are capable of actually controlling the patient's breathing itself. Humidification of the high flow oxygen air mixture from such ventilators is generally accomplished by auxiliary equipment. Again, the auxiliary equipment itself is highly specialized and expensive. Although that portion of the equipment that is directly connected to the patient is often disposable, it too may be costly.

Accordingly, it is an object of the present invention to provide for humidification of a high flow rate breathing mixture with methods and apparatus that minimize or avoid above mentioned problems.

SUMMARY OF THE INVENTION

In carrying out principles of the present invention in accordance with a preferred embodiment thereof, an adaptor nipple extends through a humidifier mixture flow chamber to the heated bottom of the chamber and connects to a sealed water container to flow water from the container to the bottom of the chamber, where it is vaporized. The high flow rate breathing mixture flows through the chamber and entrains water vapor. Feed and vent holes are provided at different levels in the bottom of the nipple adjacent the bottom of the chamber to control the level of water in the bottom of the chamber.

In a specific embodiment the bottom of the nipple is provided with a relatively lower and smaller feed orifice through which water from the container flows into the bottom of the flow chamber, and is also provided with a relatively larger and somewhat higher vent orifice that operates, when uncovered, by a lowering of the water level, to allow air to flow through the nipple and into the water container.

BRIEF DESCRIPTION OF THE DRAWINGS

FIG. 1 is an exploded pictorial illustration of a prior art nebulizer incorporating a standard water bottle, heater and mixture flow control chamber;

FIG. 2 is an exploded pictorial view similar to FIG. 1 but showing a level control nipple of the present invention in conjunction with certain components of the prior art of FIG. 1;

DETAILED DESCRIPTION OF THE PREFERRED EMBODIMENTS

Figure 9:
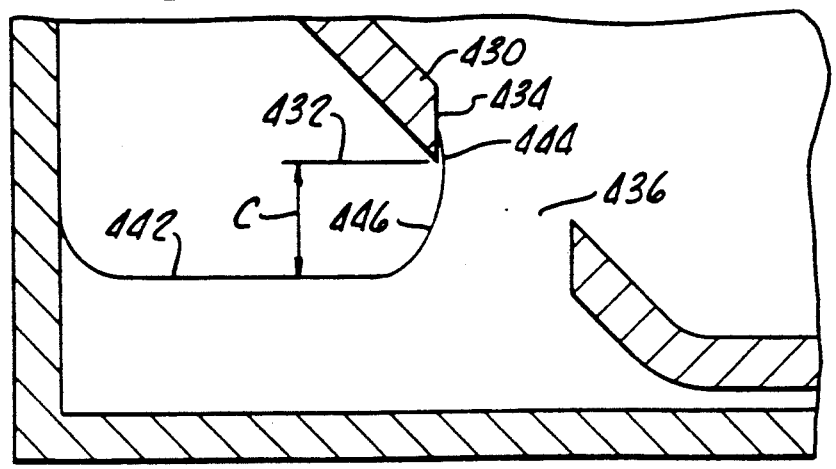

The prior art device illustrated in FIG. 1 is shown in FIG. 9 of U.S. Pat. No. 5,063,921, and comprises a nebulizer head 10 connected to an aerosol mixture flow control housing 12, which in turn is connected to a heater 14 that is mounted upon a container 16 of sterile water. In operation of the prior art nebulizer, oxygen under pressure is fed to the head 10 via a fitting 18 to cause a venturi nozzle in the head to suck up water from the container 16 via a suction tube 19 (not shown) extending from the head downwardly through the nebulizer and heater into the container. The moisturized mixture of oxygen and air is discharged from the nebulizer head via a fitting 20 and a connecting tube (not shown) to enter a fitting 22 of the flow control chamber 12, from which it is discharged via a discharge fitting 24 and tubing for connection to a patient's breathing apparatus (not shown). The flow control housing 12 is threadedly attached to heater 14. the latter includes a heated platen 26 forming the bottom of the mixture flow control chamber 12. Water and droplets from the mixing head 10 accumulate on the heater platen 26 so that water vaporized by the heated platen will be entrained in the mixture flowing through the mixture flow control chamber 12. The described nebulizer includes, as standard parts readily available in many hospitals, the nebulizer head 10, the flow control chamber 12, heater 14 and sterile water container 16.

According to principles of the present invention there is provided an adaptor nipple that enables the water container to be mounted directly above the flow control chamber and to effectively control downward flow of water from the water bottle 16 through the chamber 12 to the heater platen 26. This arrangement enables a sophisticated breathing mixture controlling ventilator to flow its output breathing mixture into mixture flow control chamber fitting 22 to be discharged, after being mixed with water vapor in the chamber, from the chamber output fitting 24.

Figure 3:
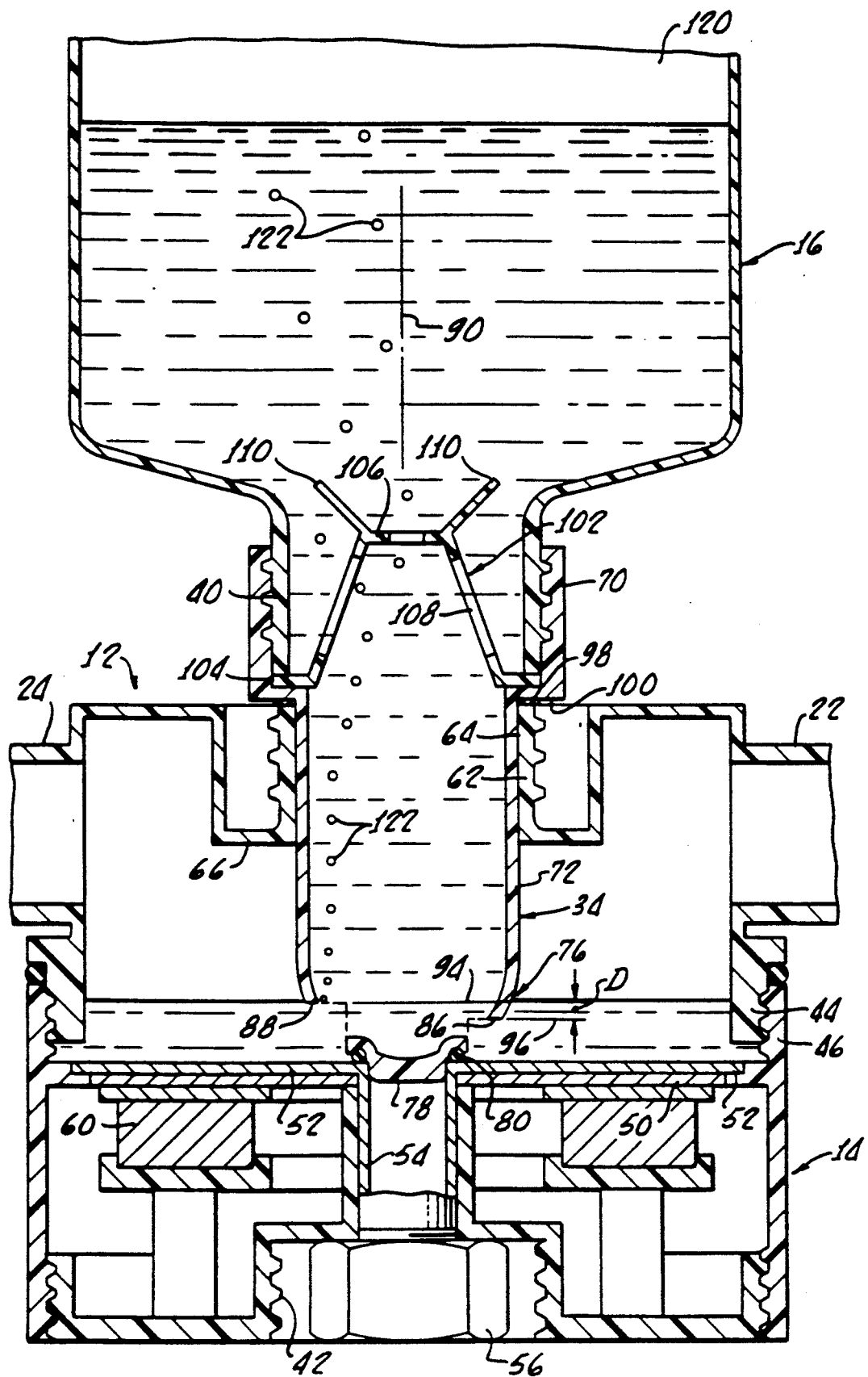
FIG. 3 is a vertical section of the assembled arrangement of FIG. 2.

In accordance with principles of the present invention, major components of the prior art nebulizer of FIG. 1 are rearranged and interconnected together with a level control adaptor nipple in the configuration illustrated in the exploded view of FIG. 2. The nebulizer head 10 of FIG. 1 is not used, but is effectively replaced by a flow generating and controlling ventilator (not shown in FIG. 2). In this arrangement the mixture flow chamber 12 and heater 14 are positioned with respect to one another in the same relation as in the prior art arrangement of FIG. 1. However, in this arrangement the water bottle 16, instead of being threadedly secured to the lower end of the heater 14, is positioned in an inverted orientation and spaced above the mixture flow chamber 12. These components, namely the mixture flow chamber 12, the heater 14 and the water bottle 16 of FIG. 2, are each individually identical to the corresponding components of the prior art of FIG. 1, but the bottle is rearranged, reoriented and positioned as shown in FIG. 2. In FIG. 2 the bottle connecting fitting 62 of the flow chamber 12 is slightly different, being recessed into the body of the chamber housing, instead of projecting outwardly as in FIG. 1. In addition, an internal wall forming a central bore of the flow chamber of FIG. 2 is shortened so as to terminate well above the platen, as shown in FIG. 3. Input fitting 22 of the mixture flow chamber 12 is connected to the output of a ventilator (not shown in FIG. 2) to receive the high flow rate breathing mixture that is produced by the ventilator. The ventilator breathing mixture, a selected mixture of air and added oxygen, flows into the chamber 12 though input fitting 22 and then, just as in the prior art, flows out from the chamber fitting 24 for connection to hoses (not shown) that lead to the patient's breathing apparatus.

The arrangement of FIG. 2 is configured to produce moist heated water vapor in the chamber 12 to be entrained by the inhalation mixture that flows through the chamber from the ventilator to the patient. To this end, water from the container 16 is caused to flow through a unique adaptor nipple 34 that is interposed between the container and the heater/mixture flow chamber subassembly. The components of FIG. 2 are illustrated in assembled condition in the cross-section of FIG. 3, which shows the input fitting 22 of mixture flow chamber 12 oriented in a diametrically opposed position with respect to output fitting 24 solely for clarity of illustration, since the actual relative positioning of the input and output fittings 22,24 is as shown in FIG. 2. Container 16 includes an externally threaded neck 40, which in the prior art arrangement would be normally threadedly received in an internally threaded fitting 42 formed in the bottom of the housing of heater 14. The internally threaded fitting 42 is not employed, however, in the arrangement of FIG. 3. The mixture flow chamber 12 includes a lower externally threaded fitting 44 that is threadedly engaged with a upper internally threaded fitting 46 in an upper part of the heater housing to securely attach the mixture flow chamber to the heater. The heater housing includes a transverse shelf 50 that supports a heater platen 52, having a central opening that connects with a centrally positioned hollow shaft 54 extending downwardly through the heater for threaded connection to a heater assembly nut 56 that holds the various heater parts together. A heater coil 60 is mounted in the heater housing just below the heater platen 52.

The standard mixture flow chamber 12 includes an upstanding externally threaded central fitting section 62, having a smooth cylindrical internal bore 64 of circular cross-section and extending for a substantial distance from the top of the mixture flow chamber structure to a recessed horizontal annular wall 66 forming part of the top of the chamber interior. In FIG. 2 the fitting section is shown recessed instead of outwardly projecting, as in FIG. 1, but application of the described inventive concepts is not affected by this fitting configuration. The central fitting section 62 and its bore 64 extend from the top of the chamber only down to the annular wall 66, well above the chamber bottom, as shown in FIG. 3. In the prior art chamber of FIG. 1 the central bore 64 extends downwardly to terminate only a very small distance from the chamber bottom (e.g. the heater platen).

The structure described to this point comprises the standard configuration of the water bottle 16, mixture flow chamber 12 (with minor changes) and heater 14 of the prior art.

In order to interconnect these standard elements and to cause them to operate as a heater/humidifier for reception and humidification of a ventilator output, nipple 34 is provided. The nipple has an upper end carrying an internally threaded fitting 70 that is adapted to threadedly receive the externally threaded neck of the water bottle 16. The body of the nipple comprises an elongated right circular cylindrical section 72 that is fixed to or integrally formed with the threaded upper water container connecting fitting 70. The nipple has a lower end, generally indicated at 76, having an outwardly (downwardly as seen in FIG. 3) projecting circular plug 78 that is received within and sealed against the interior of tubular shaft 54 that extends through the heater. Thus the bottom of mixture flow chamber 12, which is formed by the heater platen 52, is sealed by the nipple plug 78. An o-ring 80 is provided to circumscribe plug 78 in a circumferential recess in the nipple bottom that extends around the plug to assist in the sealing action.

Figure 4:
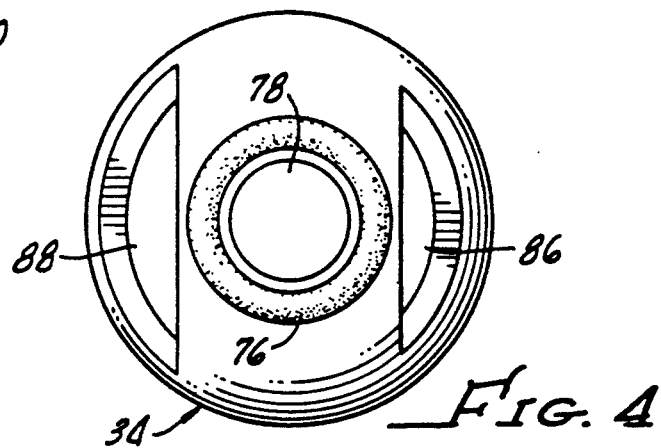
FIG. 4 is a bottom view of the nipple, showing the feed and vent holes.

The lower end of the nipple is formed with a feed aperture 86 and a vent aperture 88. As can be seen in FIG. 4, feed aperture 86 is somewhat smaller than vent aperture 88. Importantly, as seen in FIG. 3, the uppermost portion of the vent aperture 88 is higher than the uppermost portion of feed aperture 86. It is to be understood, of course, that in operation the apparatus is placed with the bottom of the heater on a horizontal surface so that an axis 90 extending longitudinally through the assembly is vertical.

In FIG. 3 line 94 indicates the level of the uppermost portion of vent aperture 88, and line 96 indicates the uppermost portion of the feed aperture 86. This illustrates the fact that the uppermost portion of the vent aperture 88 is higher than the uppermost portion of the feed aperture 86 by an amount indicated by distance D in the drawings, as will be explained below.

The smooth cylindrical outer surface of body section 72 of nipple 34 is snugly and sealingly received within the smooth interior cylindrical bore 64 of fitting 62 of the mixture flow chamber, and thus provides a hand tight sealing fit of the nipple within the chamber bore. In addition, an o-ring 98 is mounted between the uppermost end of chamber fitting 62 and a downwardly facing shoulder 100 on the bottle connecting fitting 70 of the nipple to ensure proper sealing. The sliding interfitting relationship of the nipple body section 72 and the bore 64 of the mixture flow chamber enables the nipple to be rapidly and smoothly inserted into the bore of the chamber and removed therefrom. It is important, as will be described below, that the nipple be rapidly insertable into the chamber to prevent excess water from entering the interior of the mixture flow chamber 12 during insertion.

A baffle 102 in the form of a spider includes an annular base 104 connected to annular upper baffle section 106 by a plurality of inclined circumferentially spaced baffle legs 108, with a plurality of circumferentially spaced baffle fingers 110 extending upwardly and outwardly (as seen in FIG. 3) from the annular section 106. Baffle base 104 is suitable secured in the lower end of bottle connector fitting 70 at the upper end of the nipple.

In use of the apparatus illustrated in FIG. 3, the mixture flow chamber 12 is threadedly attached to the upper end of the heater 14. The water bottle 16, in an upright position with its neck pointed upwardly, has the nipple 34 secured thereto by inverting the position of the nipple to cause its connector fitting 70 to face downwardly. The fitting 70 is then threaded onto the threaded neck of the filled water bottle, which is thus sealed to the nipple by the threaded interengagement of the bottle neck and the nipple fitting. Now the subassembly of water bottle with the nipple attached thereto is inverted, and the nipple is rapidly and slidably inserted into the smooth upwardly extending bore 64 of the chamber fitting 62 to seat shoulder 100 and o-ring 98 upon the upper edge of the fitting 62. In this position the fitting plug 78 at the fitting lower end enters and seals the interior of heater shaft 54, and o-ring 80 seats upon and seals an inner circular portion of the heater platen 52. The latter forms the bottom of the mixture flow chamber. As the bottle and nipple are inverted and as the nipple is inserted rapidly through the opening of the chamber, water from the container rapidly fills the nipple and flows outwardly through both the feed and vent holes 86,88 to cover the heater platen that forms the bottom of the chamber.

The inversion of the bottle tends to provide a rapid rush of water from the container outwardly through its neck. To restrain and restrict this sudden flow at the time of inversion the restrictor baffle 102 is provided so that water flows at a considerably slower rate from the bottle and nipple as they are inverted. The nipple is rapidly inserted into the chamber opening, and, accordingly, relatively little water will flow into the chamber through the nipple orifices during the initial rapid insertion of the nipple into the chamber. It is important that the nipple be rapidly insertable into the chamber. This is accomplished by the simple straight forward axial sliding action by which the nipple is received within the chamber bore. If this were to be made a threaded connection, the time required to complete the threaded rotation might be so great that an unacceptably large amount of water would be fed to the chamber interior before the vent hole 88 is closed by the water in the chamber.

As water flows out of the container and nipple, a vacuum is formed in the sealed head space 120 at the top of the now inverted container 16. This lowered pressure tends to restrain downward flow of water into the chamber. However, air under atmospheric pressure enters the feed and vent holes 86,88 during the very early part of the insertion procedure. As soon as the water level on the platen 52 rises above the uppermost end of the feed hole 86 (which is lower than the uppermost part of vent hole 88), air no longer flows into this feed hole, but water continues to flow from the feed hole into the body of water on the heater platen. Water also flows outwardly of the nipple through the vent hole 88. As the water level continues to rise, air continues to enter vent hole 88, flowing in the form of bubbles 122 upwardly through the hollow nipple and through the water in container 16 to the head space 120, thereby decreasing to some extent the magnitude of the negative pressure or vacuum caused by the flow of water from the container. The container bottom (which is now the uppermost portion of the inverted container) is fully sealed so that neither air nor water can flow in or out of the head space 120. When the water level on the platen 52 reaches the level of line 94, which is the uppermost portion of the upper vent hole 88, venting air can no longer enter the nipple. Thus, a balanced condition is attained in which ambient atmospheric pressure within the flow chamber is balanced against the combination of the head of water above the water level 94 combined with the negative pressure within head space 120. In this equilibrium or balanced condition there is a small and predetermined amount of water in the bottom of the chamber on the heater platen, up to level 94.

The heating element 60 of the heater may now be activated to heat the platen, and the input fitting 22 of the mixture flow chamber is then connected to the output of a ventilator. A mixture of air and oxygen from the ventilator flows into the input fitting 22 of chamber 12 at a flow rate controlled by the ventilator, flows through the interior of the mixture flow chamber over the surface of heated water contained in the bottom of the chamber on the heater platen, and then is discharged outwardly from fitting 24 to the patient's breathing apparatus. The heated platen heats the water to cause vaporization of the water and produce water vapor that is entrained in the air flowing through the chamber. Thus the ventilator controls the amount and flow rate of breathing mixture, and this breathing mixture produced by the ventilator is mixed with heated water vapor in the mixture flow chamber as it is transported to the patient.

A level of water at the height indicated at water level 94 is determined as being an optimum water level for most efficient transfer of heat from the heater platen to the water and the most efficient vaporization of water on the heater platen. It is important to allow this level to vary as little as possible if optimum vaporization is to be accomplished. A greater height of water could mean a slower rate of transfer of heat from the heater and, therefore, a slower vaporization of the water, whereas a lower level of water could result in rapid heating and a complete vaporization of all water so that a dry or non-vaporized breathing mixture might be provided. For these reasons it is important to maintain a predetermined level of water on the heater platen, a level that varies as little as possible while continuing to replenish water vapor that is carried away in the discharged breathing mixture. The described adaptor nipple and overall apparatus configuration efficiently, simply and inexpensively accomplishes these results in the following manner.

As the heated water is vaporized the water level decreases. As the water level decreases the lower feed orifice 86 remains covered by the water, but an upper portion of the vent orifice 88 is uncovered by the falling water level. As a portion of this vent orifice 88 is uncovered, ambient air from the interior of the chamber can once again bubble into the interior of the nipple and bubble upwardly through the water to the head space 120, thus relieving the negative pressure within the head space and allowing water from the container to feed through the nipple and through the feed hole 86 to the heater platen at the bottom of the mixture flow chamber. Water may also flow into the chamber through the vent hole. Thus, whenever the water level is below the uppermost level of vent hole 88 there is a continuous flow of water outwardly of the nipple through the feed orifice and a flow of air inwardly through the nipple to the head space 120 to permit the outward flow of water. As the water continues to flow from the container the water level within the chamber rises. When the water level again reaches the uppermost portion of the vent orifice 88, at level 94, the equilibrium pressure condition is again reached and water no longer flows from the container and nipple. The apparatus continues to heat the water which is vaporized to lower the level, whereupon the water within the chamber is replenished as previously described until the equilibrium condition is again reached. This cycle continues to be repeated, but with very small (not more than about $\frac{1}{8}$ inch) variation in water level. If the vent orifice did not have any portion above the feed orifice, the variation in water level would be much greater, in the order of $\frac{3}{4}$ inch, resulting in greatly decreased efficiency of vaporization, and, possibly, even some periods where the platen might be dry.

Where the breathing mixture is provided to a patient positioned in a relatively large breathing enclosure, such as for example an oxygen tent or in an incubator arrangement that encloses the entire body of an infant, there is generally a relatively steady constant pressure within the mixture flow chamber 12 and also a constant flow rate of breathing mixture provided by the ventilator. Under such conditions, the vent orifice may be made relatively large and will control variation in water level to about 0.125 inches. For example, the feed orifice may have an area of approximately 0.01 square inches, and the larger vent orifice for such stable conditions may have an area of about 0.13 square inches, with a height of about 0.47 inches above the bottom of the nipple interior. The height of the smaller feed orifice is less than about 0.10 inches. However, where the output is provided to a small volume breathing area, such as to the smaller volume interior of a breathing mask that is fitted to a patient's head, the breathing of the patient himself may be sufficient to cause significant pressure variations within the breathing tube and therefore within the mixture flow chamber 12. Similarly, in certain therapy conditions the ventilator may be arranged to produce a varying flow rate and/or varying pressure. Variations in pressure and/or flow rate within the chamber 12, where the vent orifice is relatively large, will result in unacceptably large fluctuations (greater than 0.125 inches) of water level within the chamber 12. This is due to the fact that the level control provided by the feed and vent orifices is sensitive to the ambient pressure (e.g. pressure within the mixture flow chamber 12), and thus may be subject to relatively large fluctuation. Accordingly, for such dynamic conditions (where the apparatus is subject to relatively large pressure and/or flow rate fluctuation) the vent orifice 88 will be made smaller. Thus, for such a dynamic situation feed orifice 86 may have an area of about 0.01 square inches and vent orifice 88 may have an area of about 0.07 square inches, with a height above the nipple of about 0.30 inches. The height of the smaller feed orifice is the same for both static and dynamic configurations, less than about 0.10 inches. This smaller vent orifice will result in a water level variation (and the described more dynamic conditions) of about 0.125 inches.

If deemed necessary or desirable, in order to allow a single apparatus or single nipple to accommodate both static and dynamic conditions the effective size of the vent orifice 88 may be adjustably varied.

Figure 6:
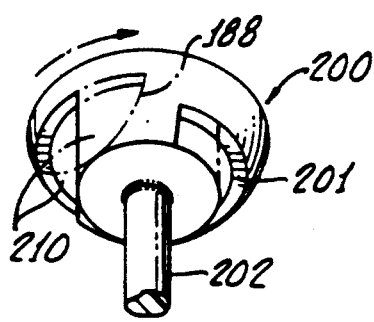
FIG. 6 is a pictorial illustration of the orifice adjustment member of FIG. 5.
Figure 5:
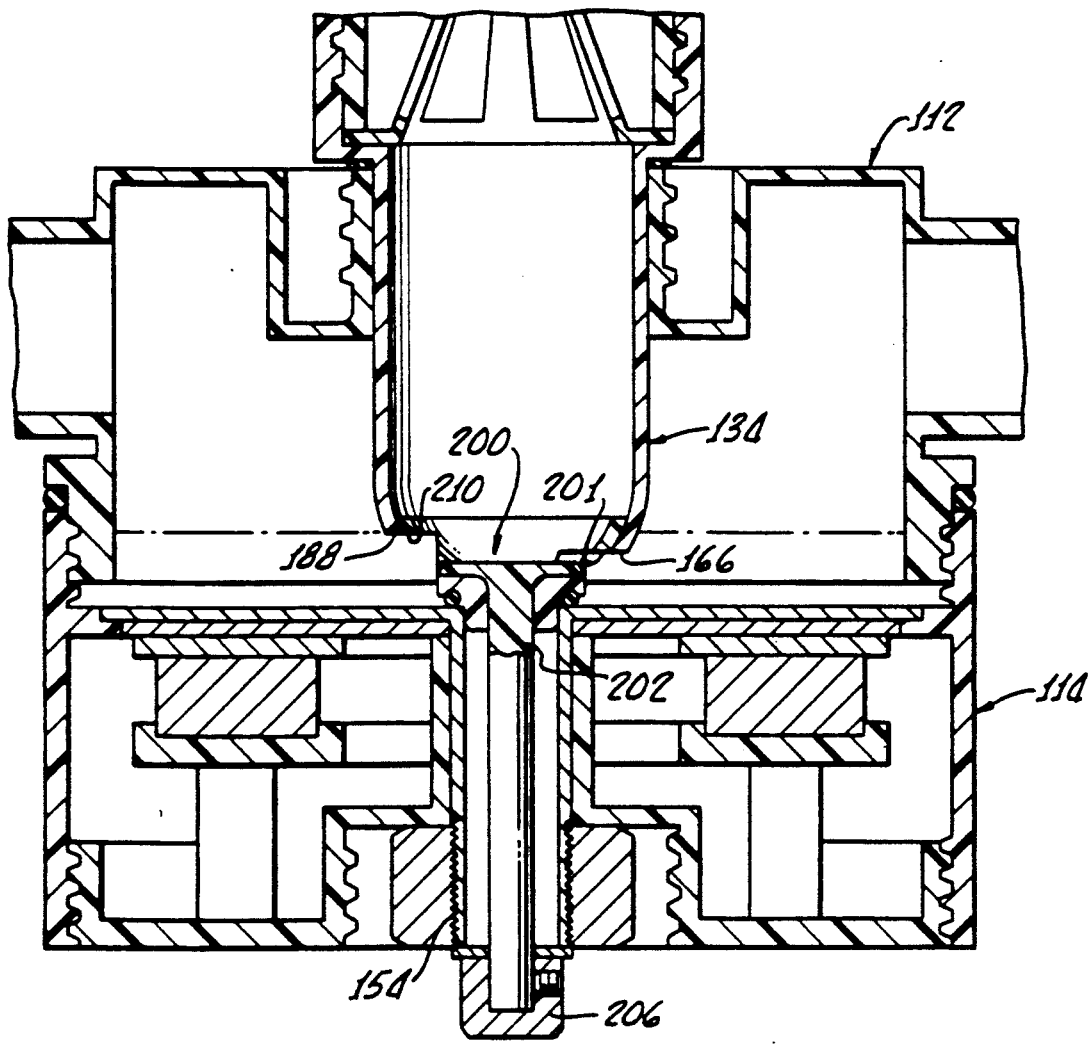
FIG. 5 is a view similar to that of FIG. 3 showing part of a modified form of liquid level control.

Illustrated in FIGS. 5 and 6 is an arrangement for varying the effective size of the vent orifice. Feed orifice size is not varied. In these figures the water container (not shown) is connected by a nipple 134 to a mixture flow control chamber 112 that is mounted on a heater 114. All of the parts are identical to the corresponding parts described in the prior figures. The sole difference is that an adjustment member 200, having an exterior configuration that mates with the interior of the lowermost end of the nipple 134, is rotatably mounted in the lower end of the nipple and is fixed to a shaft 202 having a knurled operating handle 206. Shaft 202 extends through the hollow shaft 154 of the heater housing to the bottom of the heater so that the knob 206 may be accessible to a user for rotation of shaft 202 and adjustment member 200. Adjustment member 200 (FIG. 6) includes an adjustment vent orifice 210 and a similar larger adjustment feed orifice 201 on an opposite side of the member 200. The adjustment member is configured and arranged so that only the vent orifice 188 of the nipple may be closed by the adjustment member 200. This is the position shown in FIG. 6, wherein the dotted line 188 represents the nipple vent orifice which is partly covered by the adjustment member. Rotation of the knob 206 will rotate adjustment member 200 so that adjustment vent orifice 210 overlaps partly or completely with the primary vent orifice 188 formed in the bottom of the nipple, as indicated in FIG. 6. When adjustment vent orifice 210 is positioned so that primary vent orifice 188 is either partly or fully open the additional feed orifice 201 in the adjustment member always fully uncovers the nipple feed orifice 186 so that the feed orifice size does not change. The larger adjustment member feed orifice 200 is large enough so that is never even partly occludes the nipple feed orifice throughout the range of adjustment of the member. Accordingly, in different positions of rotation of adjustment member 200 the vent orifice area may be either opened partially or completely so as to create either a large opening humidifier for static conditions or a small opening humidifier for dynamic conditions.

Figure 7:
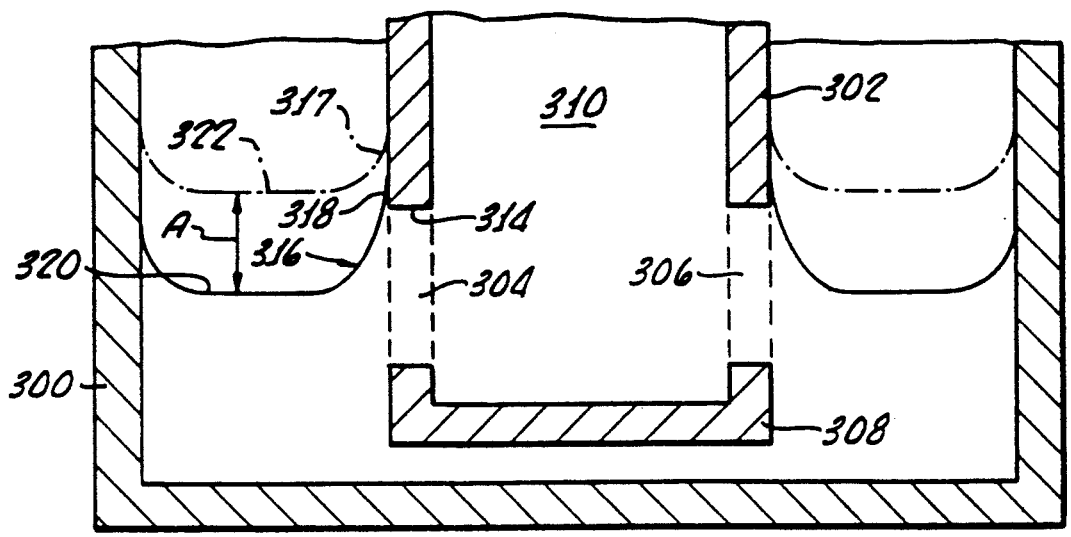
FIGS. 7, 8, and 9 are partial schematic illustrations useful in explaining action of the water meniscus at the vent hole of the adaptor nipple.

The shape and orientation of walls that define the vent hole is important in control of water surface meniscus, and therefore of water level variation, as will be explained in connection with the schematic illustration of FIGS. 7-9. FIG. 7 is a schematic illustration of a vessel 300 that receives the end of a tube 302 having apertures 304,306 which do not extend fully circumferentially around the tube and which tube has a bottom portion 308. Relative heights of apertures 304,306 are not important to the explanation based on FIG. 7. Assume the interior 310 is filled with water, which accordingly flows outwardly through the holes 304,306 to fill the interior of vessel 300 until the water level reaches the upper end 314 of the aperture 304. It is assumed that tube 310 connects to a body of water in a sealed container, and accordingly the tube 302 and the container (not shown) are functionally analogous to Applicant's adaptor nipple 304 and container 16. As the water level drops from a level at or above the top 314 of aperture 304, a meniscus 316 forms on the water surface because of the surface tension of the water, causing the meniscus to have a point of attachment 318 to the exterior wall of tube 302. The meniscus follows the relatively large radius curvature indicated at 316 until it reaches the horizontal water level 320, as illustrated in the drawing. The meniscus comprises an outer surface of the water at or around the aperture 304. Although the drawing is not to scale, it is intended to show that there is a distance A between a horizontal line 322 at the height of the upper end of the meniscus 318, where it attaches the to wall of the tube, and the water level 320. This is a relatively large distance. As the water level drops still further, the meniscus 318 will suddenly detach itself from the wall of the tube at the upper portion 314 of its opening 304, and the entire area of hole 304 above the water level 320 suddenly opens to allow relatively large quantities of air to bubble upwardly through the water filled interior 310 of tube 302. At the same time water from the container and interior of the tube to pass outwardly through the opening 304. It is to be emphasized that in actuality the distance "A" is relatively large when the wall of tube 302 is vertical. Thus, there is a relatively large fluctuation of water level because the water drops from a level approximately at the upper end 318 of the meniscus to a considerably lower level before the meniscus detaches itself from the tube wall.

This relatively large change in water level causes significantly less efficient operation of the heater. As previously explained, the system operates to cause the nipple or tube 302 to refill vessel 300 and bring the water level in the chamber back up to a level 322 at the top 314 of the opening 304. Thus a relatively large quantity of water is added to thereby drop the temperature of the water already in the chamber. This decreases the rate of vaporization and puts a greater load on the heater, which now has to heat a relatively large quantity of cooler water. For this reason, namely the efficiency of heater operation and efficiency of water vaporization, it is desirable to minimize the change in level of the water in the chamber. Applicant has discovered that by inwardly tapering the wall of the tube in which the opening is formed, the change in water level can be significantly decreased. Thus, as schematically illustrated in FIG. 8, a wall 330 of the tube or nipple (only one wall of the hollow tube nipple is shown in FIG. 8) is inclined downwardly and inwardly. Although a straight inclination is shown in FIG. 8 and an inwardly and downwardly curving bottom portion is shown in FIGS. 3 and 5, it will be readily understood that the concept of the operation of the tube or nipple wall remains the same. As previously mentioned, the nipple or tube operates to feed water to the chamber or vessel until the water level reaches a height indicated at 332, which is substantially at the uppermost edge 334 of the vent opening 336. Vent opening 336 represents and is analogous to the vent opening 88 of applicant's nipple as shown in FIG. 3. In equilibrium position the water is at level 332 and the apertures of the nipple are covered with water so that no water can flow from the sealed container into the chamber.

With the water level at level 332 the water forms a meniscus generally indicated at 340. As the water level drops to a level such as, for example, that indicated at 342, the uppermost portion of the meniscus at 344 still adheres to the wall 330 but is just at or above the upper portion 334 of the wall. The water now forms a meniscus 346 similar to the meniscus 316 of FIG. 7. However, it will be noted that the meniscus 346 formed by the water adhering to the inwardly and downwardly inclined wall 330 has a much sharper curvature than the meniscus 316 of FIG. 7. This is due to the inward inclination of the outer surface of wall 330. Because of this sharper curvature of the meniscus 346 the water reaches a higher level 342 (closer to the top 334 of hole 336) before the upper portion 344 of the meniscus will detach itself from the wall 330. The distance between the level 332 at which the aperture 336 is fully closed and the water level 342 at which the aperture 336 opens is indicated in the drawing as equal to "B". This distance "B" is significantly less than the distance "A" at the vertical wall opening 304 of FIG. 7. In other words, with the inwardly inclined wall 330 the water level will not drop nearly as far as it would if the wall in which the opening 336 is formed were to be vertical (as illustrated in FIG. 7). Thus the inclination of the nipple wall enables the water level to be maintained with a significantly decreased variation in the level. As mentioned above, this greatly increases the efficiency of the heater and the efficiency of the water vaporization. Of course whether the inclined wall is straight, as indicated in FIG. 8, or curved as indicated in FIGS. 3 and 5, the meniscus still has a sharper curvature and thus allows less fluctuation in water level.

Figure 8:
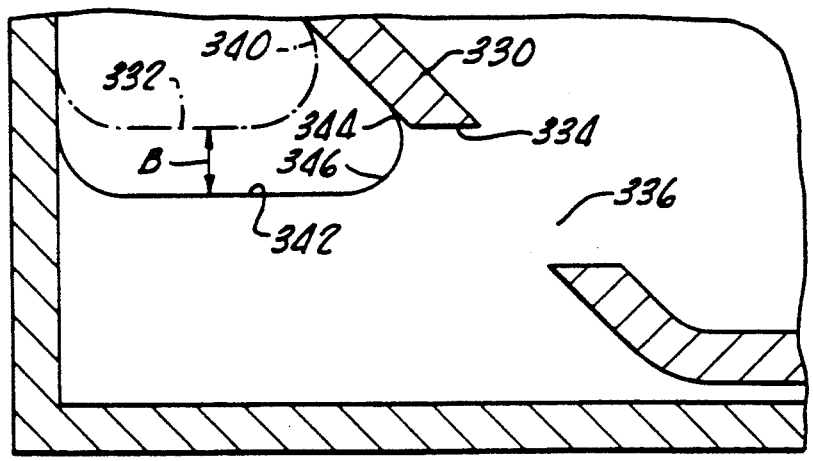

Not only is it important, from the standpoint of minimizing water level fluctuation, to have the nipple wall 330 inclined inwardly and downwardly, but it is important that the upper edge 334 of the opening 336 be horizontal, as shown in FIG. 8.

To explain the need for the horizontal edge of the vent opening, FIG. 9 is provided to show an opening 446 in an inclined wall 430, where both the wall and hole are analogous to comparable elements of FIG. 8. In the arrangement of FIG. 9, however, the edge 434 of the hole 436 is made vertical, thereby creating a meniscus as indicated at 446. The meniscus 446 adheres to the vertical surface of the edge 434 of hole 436 and has a curvature of a larger radius. Accordingly, the water level, with the arrangement of FIG. 9, will fall to a level 442 that is a greater distance "C" below the level 432 at which the opening 436 is normally closed. At the water level 442 indicated in FIG. 9, the meniscus upper end 444 will detach itself from the vertical wall 434 to allow a relatively large amount of air into the nipple, and, of course, to feed water from the nipple into the chamber, to thereby again raise the water level to the level 432 where it closes the opening 436. As previously described in all of these arrangements, when the openings are closed by the water level, the sealed upper portion of the water container has a pressure sufficiently low that, together with the head of water in the container and nipple, balances atmospheric pressure.

It may be noted that the area of the feed orifice may be relatively small (about 0.01 square inches) because this orifice is intended to feed water at all times. The vent orifice, on the other hand, must be uncovered by the falling water level to provide vent air to the container. Therefore the vent orifice is made within a larger area (about 0.50 square inches in static condition) to be sure that it is large enough to cause the meniscus to fall away from the upper edge of the opening. In a dynamic condition of varying pressure within the chamber, dynamic conditions assist in pulling the meniscus away from the vent opening, so that a smaller vent opening (about 0.07 square inches) may be used for dynamic conditions. The feed opening area (about 0.01 square inches) need not be different for static and dynamic conditions.

As described above, the operation of the unit is simple. Flow from the ventilator unit passes through the chamber to entrain water vapor produced by the water that is heated by the heater as the water vapor is carried away in the air stream and delivered to the patient. Water level lowers as the vapor is carried away until the vent hole is exposed. With the vent hole exposed, water is again fed from the feed hole, thereby raising the water level and resealing the vent hole.

The unit is widely adaptable to handling a large range of flow rates, from relatively low flow rates to very high flow rates, as produced by a conventional ventilator machine. Yet, the apparatus is simple, utilizing standard inexpensive and readily disposable parts.

It will be seen that there has been provided a simple, inexpensive and easily assembled adaptor nipple that is available for use with standard readily available humidifier or nebulizer heater, flow chamber and water bottle components and enables assembly of these standard components in a simple and effective arrangement for providing heated and humidified air to the output of a ventilator.

I claim:

1. A humidifier for heating and vaporizing water for mixing with a breathing mixture comprising:
   a heater having:
     a heater housing
     a heater platen extending across the heater housing, and
     a heating element mounted in the housing adjacent the heater platen,
   a breathing mixture flow housing comprising:
     means for defining a flow chamber having input and output ports,
     means for connecting the chamber to the heater housing adjacent the heater platen,
     a liquid container, and
     a nipple receiving bore extending from the interior of said chamber to the exterior of said mixture flow housing, and
   a flow control nipple having:
     an elongated hollow cylindrical body having a smooth exterior surface slidingly and sealingly received in said bore, a rounded closed bottom end having an inwardly and downwardly tapered side wall, and an upper end,
     a fitting mounted to said upper end and configured and arranged to rigidly connect said body to said liquid container, whereby said container and nipple can be inverted and inserted as a unit into said bore with said nipple in said flow housing and said container mounted to said flow housing through said nipple,
     a feed hole formed in said bottom end tapered wall, and
     a vent hole formed in said bottom end tapered wall and spaced from said feed hole, said vent hole having an uppermost hole boundary that is positioned further from said bottom end than said feed hole, said nipple having an interior defining a single common passage for air and water extending from said feed and vent holes to said fitting.

2. The humidifier of claim 1 wherein said vent hole uppermost hole boundary is defined by a surface extending horizontally through said tapered wall.

3. The humidifier of claim 1 including a flow restricting baffle positioned in said container connection fitting.

4. The humidifier of claim 1 wherein said bore in said chamber includes a smooth cylindrical surface, and wherein said nipple exterior surface mates with and is slidably received in said bore, and means for sealing said nipple to said flow housing.

5. The humidifier of claim 1 wherein said feed hole comprises a relatively small feed orifice having an uppermost portion, and wherein said vent hole comprises a vent orifice larger than said feed orifice and having a horizontal wall forming an uppermost boundary of said vent orifice positioned above the uppermost portion of said feed orifice.

6. The humidifier of claim 5 including adjustable means movably mounted to said nipple for varying the area of said vent hole.

7. The humidifier of claim 6 wherein said adjustable means comprises a rotatable closure member mounted for rotation within said nipple at the lower end thereof, a vent adjustment orifice mounted in said rotatable closure member, and a shaft connected with said rotatable closure member and extending through said heater passage for adjustment of said closure member.

8. A humidifier comprising:
   a heater having:
     a heater housing
     a heater platen extending across the heater housing, and
     a heating element mounted in the housing adjacent the heater platen,
   a breathing mixture flow housing comprising:
     means for defining a flow chamber having input and output ports,
     means for connecting the chamber to the heater housing adjacent the heater platen, and
     a nipple receiving bore extending from the interior of said chamber to the exterior of said mixture flow housing, and
   a flow control nipple having:
     a body portion extending into said nipple receiving bore,
     an upper end having a container connection fitting,
     a lower end in said chamber,
     a feed hole formed in said lower end,
     a vent hole formed in said lower end and having an upper portion positioned above said feed hole, said feed hole comprising a relatively small feed orifice having an uppermost portion, and said vent hole comprising a vent orifice larger than said feed orifice and having an upper portion positioned above the upper portion of said feed orifice, and
     adjustable means movably mounted to said nipple for varying the area of said vent hole, said heater including a passage extending through said heater housing and through said platen, said nipple including a plug positioned at the lower end of the nipple for sealing said heater passage.

9. A humidifier comprising:
   a flow housing including a vaporizing chamber having a gas input and a humidified gas output, and a bore extending from said flow housing,
   means for forming a bottom for said chamber,
   means for heating said bottom forming means,
   a closed container of liquid positioned above said vaporizing chamber, and a level control nipple for flowing liquid from said container to said chamber and for controlling level of liquid in said chamber, said level control nipple comprising:
  an elongated hollow cylindrical body having a smooth exterior surface slidingly and sealingly received in said bore, a rounded closed bottom end having an inwardly and downwardly tapered side wall and an upper end,
  a fitting mounted to said upper end and configured and arranged to rigidly connect said body to said liquid container, whereby said container and level control nipple can be inverted and inserted as a unit into said bore with said nipple in said flow housing chamber and said container mounted to said flow housing through said nipple,
  a feed hole formed in said bottom end tapered wall, and
  a vent hole formed in said bottom end tapered wall and spaced from said feed hole, said vent hole having an uppermost hole boundary wall that is positioned further from said bottom end than said feed hole, sand vent hole uppermost hole boundary wall being defined by a surface extending horizontally through said inwardly and downwardly tapered wall.

10. The humidifier of claim 9 wherein said means for heating said chamber bottom comprises a heater, said heater including a housing, a heating element mounted in said housing, and a heater platen adjacent said heating element, said heater platen forming said bottom of said vaporizing chamber, and means for coupling said heater housing to said vaporizing chamber.

11. The humidifier of claim 9 including means for adjusting the size of said vent orifice.

12. The humidifier of claim 11 wherein said means for adjusting comprises a closure member rotatably mounted within said nipple at the bottom portion thereof, said closure having first and second adjustment orifices, and means for adjustably positioning said adjustment member.

13. A humidifier comprising:
  a heater having:
    a heater housing
    a heater platen extending across the heater housing, and
    a heating element mounted in the housing adjacent the heater platen,
  a breathing mixture flow housing comprising:
    means for defining a flow chamber having input and output ports,
    means for connecting the chamber to the heater housing adjacent the heater platen, and
    a nipple receiving bore extending from the interior of said chamber to the exterior of said mixture flow housing, and
  a flow control nipple having:
    a body portion extending into said nipple receiving bore,
    an upper end having a container connection fitting,
    a lower end in said chamber,
    a feed hole formed in said lower end, and
    a vent hole formed in said lower end and having an uppermost portion positioned above said feed hole, said heater including a passage extending through said heater housing and through said platen, said nipple including a plug positioned at the lower end of the nipple for sealing said heater passage.

14. A humidifier for heating and vaporizing water for mixing with a breathing mixture comprising:
  a breathing mixture flow housing comprising:
    means for defining a flow chamber having input and output ports, having an open top and an open bottom with a threaded heater connection at said bottom, and a threaded container connection fitting at said top,
  a heater having:
    a heater housing,
    a heater platen extending across the heater housing and forming a bottom of said breathing mixture flow housing, and
    a heating element mounted in the heater housing adjacent the heater platen, and
    a threaded heater fitting threadedly interengaged with the threaded heater connection of said breathing mixture flow housing,
  a unitary combination of a standard water container having a standard connection neck and an adapter flow control nipple having a threaded fitting threaded upon and sealed to the connection neck of the water container and having a nipple body, said combination of adapter nipple and water container being adapted to be inverted as a unit and connected to flow water from said container to said heater platen and to control the level of water on said heater platen, said breathing mixture flow housing including a nipple receiving bore extending from the interior of the flow chamber to the exterior of the mixture flow housing, said flow control nipple including an elongated hollow cylindrical body having a smooth exterior surface slidingly and sealing received in said bore, whereby said nipple and water container are readily and rapidly attachable to said flow housing and heater housing, said nipple cylindrical body having a rounded closed bottom end and an inwardly and downwardly tapered wall,
  a feed hole formed in said bottom end tapered wall, and
  a vent hole formed in said bottom end tapered wall and spaced from said feed hole, said vent hole having an uppermost hole boundary that is positioned further from said bottom end than an uppermost portion of said feed hole.

* * * * *